US00PP20120P3

(12) United States Plant Patent
Kuramochi

(10) Patent No.: US PP20,120 P3
(45) Date of Patent: Jun. 23, 2009

(54) ***LIPPIA* PLANT NAMED 'CAMPAGNA VERDE'**

(50) Latin Name: *Lippia nodiflora L.*
Varietal Denomination: Campagna Verde

(76) Inventor: Hitoshi Kuramochi, Nice-Urban Higashi-Mine #401, 3029-5 Higashi-Mine Machi, Utsunomiya, Tochigi (JP), 321-0944

( * ) Notice: Subject to any disclaimer, the term of this patent is extended or adjusted under 35 U.S.C. 154(b) by 152 days.

(21) Appl. No.: 11/257,652

(22) Filed: Oct. 21, 2005

(65) Prior Publication Data

US 2006/0059595 P1 Mar. 16, 2006

(30) Foreign Application Priority Data

Mar. 15, 2004 (JP) ..... 12041
Dec. 13, 2004 (JP) ..... 17741

(51) Int. Cl.
*A01H 5/00* (2006.01)

(52) U.S. Cl. ..... Plt./263.1
(58) Field of Classification Search ..... Plt./263.1, Plt./226
See application file for complete search history.

*Primary Examiner*—June Hwu

(57) ABSTRACT

A new cross-species hybrid within the Verbenaceae family, named 'Campagna-Verde', having superior vigor and suitability for use as a groundcover, as characterized by fast growth rate, prostrate growth habit forming a dense mat, absent or rare production of seeds, resistance to low and high temperature extremes, resistance to high salinity, resistance to low and high pH extremes, resistance to arid and humid conditions, good tolerance to trampling, and resistance to diseases and pests.

1 Drawing Sheet

Figure 1:
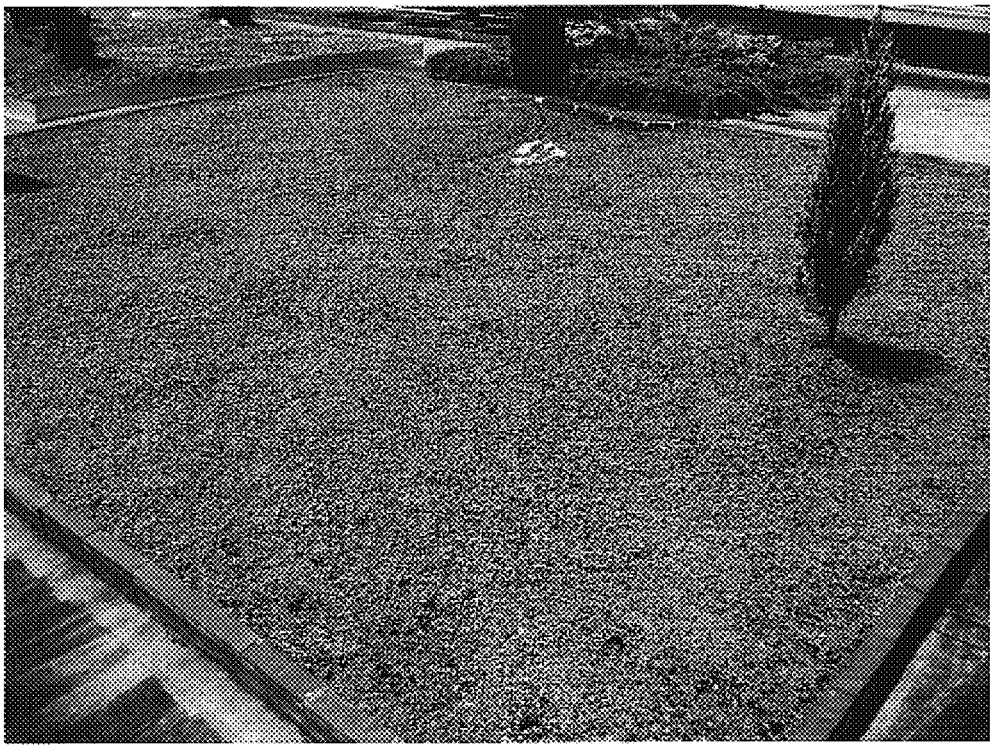

Botanical classification: *Lippia nodiflora L.*
Variety denomination: The new Verbenaceae family groundcover variety denomination is 'Campagna Verde'.

BACKGROUND OF THE INVENTION

The present invention comprises a new and distinct cross-species hybrid within the *Lippia* genus of the verbena family (Verbenaceae), hereinafter referred to by the name 'Campagna Verde'.

'Campagna Verde' was developed by a controlled crossbreeding, carried out by Hitoshi Kuramochi, between two members of the *Lippia* genus of the Verbenaceae family, and selection among the resultant progeny for fast growth to cover areas, good tolerance to low temperature, good tolerance to saline conditions, good tolerance to humid and arid conditions, absent or rare production of seeds, good resistance to being trod on, good tolerance to both high and low pH extremes, and strong resistance to disease and pests. The female parent of 'Campagna Verde' used in the cross above is a patented member of the Verbenaceae family, 'S Hitoshi' (Japan Patent Registration No. 12041), with botanical classification *Lippia nodiflora* L. The male parent of 'Campagna Verde' is wild *Lippia,* known as 'Iwadaresou' and similar to *Lippia nodiflora,* originating from Nansei-Shoto, Southwestern Islands, Okinawa prefecture, Japan. Although both parents are similar to *Lippia nodiflora* L., they are distinct species from each other based on morphology and the current crossbreeding. The new hybrid was created during the period 1999–2004, with crossbreeding carried out in May 1999 and selection over the period May 1999 to May 2002, and has been repeatedly asexually reproduced at Utsunomiya University, Utsunomiya City, Tochigi Prefecture, Japan, using cuttings and layering over a two-year period. It has been found to retain its distinctive characteristics through successive generations of asexual reproduction.

BRIEF SUMMARY OF THE INVENTION

'Campagna Verde' is a groundcover interspecies hybrid of the Verbenaceae family, having superior vigor and suitability for use as a ground cover, as characterized by vigorous prostate growth to cover an area, superior resistance to low temperature, absent or rare production of seeds, and short plants. The data below, which defines the characteristics of 'Campagna Verde' and differentiates 'Campagna Verde' from its male and female parents, was collected from May 2002 to December 2003 from asexual reproductions. The plants were grown both outdoors, in plowed soil supplemented with fertilizer containing 8% N, 8% P, and 8% K, and in temperature-controlled and uncontrolled greenhouses in a mixture of Utsunomiya black soil and river sand, supplemented with the same fertilizer.

Comparison with Female Parent

Plants of the new verbena family interspecies hybrid 'Campagna Verde' are dissimilar to the female parent *Lippia nodiflora* L. 'S-Hitoshi' in growth rate, resistance to low temperature, frequency of seed production, and plant height. Plants of the new hybrid 'Campagna Verde' differed from plants of the female parent 'S-Hitoshi' in the following characteristics:

1. The new hybrid 'Campagna Verde' grows to cover an area two (2) times faster than its female parent 'S-Hitoshi'.
2. The new hybrid 'Campagna Verde' exhibits superior resistance to low temperature extremes compared to its female parent 'S-Hitoshi'.

3. The new hybrid 'Campagna Verde' does not produce seeds, in contrast to its female parent 'S-Hitoshi'.
4. The new hybrid 'Campagna Verde' exhibits plants with height of about 2.0 cm, while its female parent 'S-Hitoshi' has plants of about 2.3 cm.

Comparison with Male Parent

Plants of the new verbena family interspecies hybrid 'Campagna Verde' are dissimilar to the male parent, wild *Lippia* ('Iwadaresou') originating from the southwestern islands, Okinawa Prefecture, Japan, in growth rate, resistance to low temperature, frequency of seed production, and plant height. They are similar to the male parent *Lippia* 'Iwadaresou' in plant and growth habit, as well as leaf form, size, venation, and texture. In comparisons done at the Utsunomiya University Research Center (see above), plants of the new hybrid 'Campagna Verde' differed from plants of the male parent *Lippia* 'Iwadaresou' in the following characteristics:

1. Plants of the new hybrid 'Campagna Verde' grow to cover an area at 3.5 times the rate of plants of its male parent, *Lippia* 'Iwadaresou'.
2. Plants of the new hybrid 'Campagna Verde' exhibit superior resistance to low temperature extremes compared to plants of the male parent *Lippia* 'Iwadaresou'.
3. Plants of the new hybrid 'Campagna Verde' do not produce seeds, in contrast to plants of its male parent *Lippia* 'Iwadaresou'.
4. Plants of the new hybrid 'Campagna Verde' exhibit a height of about 2.0 cm, while plants of its male parent *Lippia* 'Iwadaresou' have a height of about 2.5 cm.

Plants of the new hybrid 'Campagna Verde' were similar to plants of the male parent *L. nodiflora* 'Iwadaresou' in the following characteristics:

1. Plants of the new hybrid 'Campagna Verde' exhibit a vigorous growing, trailing groundcover form with a procumbent growth habit, forming a dense mat; this is very similar to, or identical to, the form and growth habit of plants of its male parent *Lippia* 'Iwadaresou'.
2. Plants of the new hybrid 'Campagna Verde' have leaves with an obovate shape that is very similar to, or identical to, the shape of leaves of plants of its male parent *Lippia* 'Iwadaresou'.
3. Plants of the new hybrid 'Campagna Verde' have leaves of fairly narrow and fairly short (1.5 cm) dimensions. Leaves of plants of its male parent *Lippia* 'Iwadaresou' exhibit very similar dimensions.
4. Plants of the new hybrid 'Campagna Verde' have venation very similar to, or identical to, that of plants of its male parent *Lippia* 'Iwadaresou'.
5. Plants of the new hybrid 'Campagna Verde' have hairless leaves of a texture very similar to, or identical to, that plants of its male parent *Lippia* 'Iwadaresou'.

Comparison with Related Known Cultivars

The applicant is not aware of specific cultivars of *Lippia nodiflora* or similar plants for the purpose of groundcover other than the female parent 'S Hitoshi', which is distinguished from 'Campagna Verde' above. Commercially available groundcover *Lippia nodiflora* seems not to be distinguished from the wild or weed varieties of *L. nodiflora*. 'Campagna Verde' differs from wild *Lippia nodiflora* plants chiefly in its higher growth rate, greater cold resistance, and absence of seed production (and associated dissemination), similar to the case of its wild male parent, *Lippia* 'Iwadaresou', shown above.

BRIEF DESCRIPTION OF ILLUSTRATION

Typical specimens of the plant for the new cross-species hybrid 'Campagna Verde' are shown in the accompanying photographs. The colors shown are as true as possible within the usual limits of this kind of illustration.

Figure 2:
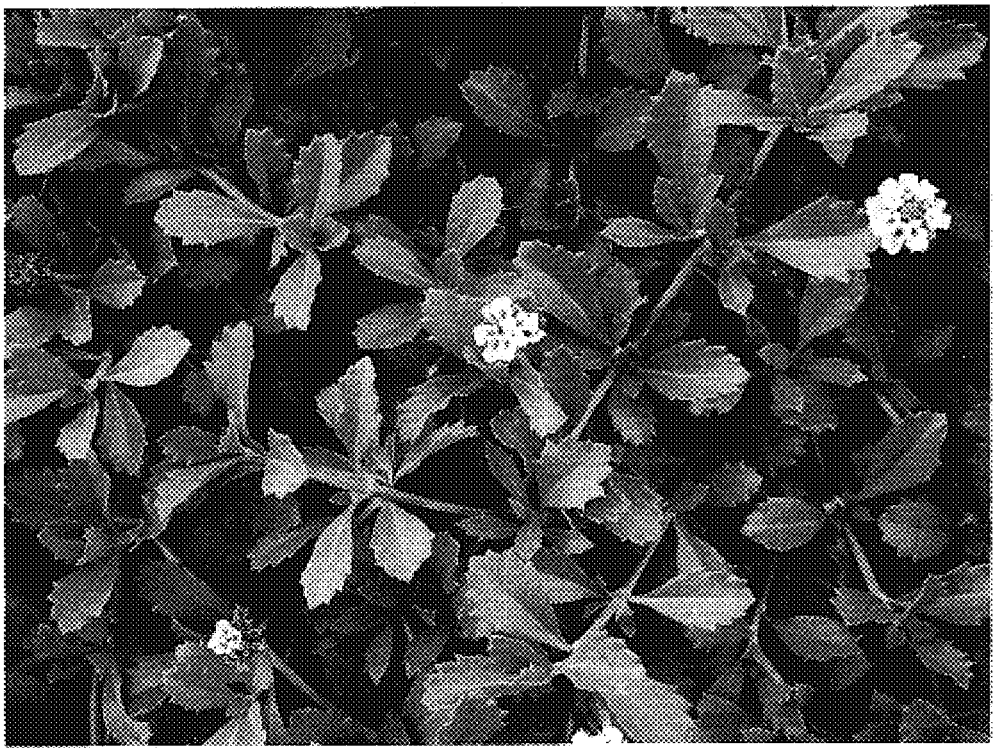

FIG. 1 is a whole plant view of the new hybrid 'Campagna Verde', covering an approximate area of 28,400 $cm^2$ (2.84 $m^2$), and FIG. 2 is a side perspective view of a typical flowering stem. The plant shown in the illustration was grown under research conditions.

DETAILED BOTANICAL DESCRIPTION

The following description of the new verbena family interspecies hybrid 'Campagna Verde' is of plants grown from asexual reproductions carried out, with data collected, at in Utsunomiya City, Tochigi Prefecture, Japan, in both a research field with plowed soil supplemented with fertilizer containing 8% N, 8% P, and 8% K, and in temperature-controlled and uncontrolled greenhouses in a mixture of Utsunomiya black soil and river sand, supplemented with the same fertilizer, in the time period May 2002–December 2003. The hybrid has not been observed under all possible environmental conditions. The phenotype might vary significantly with variations in the environment such as light intensity without any variance in genotype.

Plants of the new hybrid 'Campagna Verde' have shown excellent resistance to high and low temperature extremes, having been grown successfully under temperature conditions ranging from a gentle frost to 37 degrees Celsius. These plants also show, in separate experiments, excellent tolerance to a range of soil pH from 4.0–12.0, humid conditions, arid conditions, high salinity extremes, being trod on or trampled, and excellent resistance to common diseases and pests.

The following description is with respect to plants grown under the experimental conditions described above. The plant and flower measurements and foliage size are established as an average using standard cultural procedures. The color designations are with regard to the Horticultural Colour Chart of the Royal Horticultural Society, London, England (R.H.S. Colour Chart), as well as the colour chart of the Japan Horticultural Society (JHS).

Plant

Height (centimeters): 2.0.
Average spread: 190 cm.
Form: Vigorous growing, trailing groundcover.
Growth habit: Procumbent, forming a dense mat.
Blooming season: late May through mid-November.
Disease and pest resistance: Exhibits very little damage from most common diseases and pests; in very humid conditions mildew spotting due to *Rhizoctonia solani* and *Pythium vanterpolii* may appear and can be treated by standard commercially available pesticides.
Drought and temperature resistance: As described above, 'Campagna Verde' satisfactorily withstands temperature extremes from a gentle frost to 37 degrees Celsius, and is resistant to humid and arid conditions.
Propagation:
*Type.*—Stem cuttings and layering.

*Optimal planting period.*—Late April to mid-October.
Growth treatments or special conditions: None Foliage Stem:
*Length.*—1.5 meters average.
*Diameter.*—2 mm.
*Texture.*—Somewhat rough and hairy, not waxy; very similar or identical to wild L. nodiflora 'Iwadaresou'.
*Color.*—Dark green, brownish green, JHS 3502, near RHS 145D.
Arrangement of leaves: Opposite along the stem.
Distance between internodes: 1.6 cm.
Shape of leaf: Obovate.
Size of leaf: Width (mm): 6 mm, Length (cm): 1.5 cm.
Leaf apex shape, base shape, aspect: Obtuse, Rounded, Not sessile.
Leaf, upper, surface color: Olive green, RHS color chart No. 146B, JHS color chart No. 3508.
Leaf lower surface color: Olive green, RHS color chart No. 146B, JHS color chart No. 3508.
Leaf, surface, texture: Hairless, very similar or identical to wild *L. nodiflora* 'Iwadaresou'.
Leaf venation: Very similar or identical to wild *L. nodiflora* 'Iwadaresou'.
Leaf margin, type: Serrated.

Flower

Corolla shape: Conic (Obtuse; apex acute).
Corolla diameter: 0.6 cm.
Corolla length: 0.6 cm.
Number of corolla per inflorescence: 50.
Flower type: Single.
Inflorescence form: Terminal, spikes, on ascending stem of length 1.3 cm.
Diameter of fully expanded blossoms: 0.8 cm.
Number of flowering spikes per plant: Approximately 27.
Fragrance: None.
Color: Flower bud: RHS 69D, JHS 9501.
*Flower.*—Purplish-white; JHS No. 8901, near RHS 76A.
Seeds: Not observed.

Bract

Size: 1.5 mm length; 1 mm width.
Shape: Ovate, apex acute (conical).
Color: Yellow-green, RHS 143C, JHS 3709.

Calyx

Size: 5 mm length and width.
Shape: Linear; apex is acute ('diamond shape').
Color (both upper and lower surfaces): Yellow-green, RHS 143C, JHS 3709.

Peduncle

Average length: 3.5 cm.
Surface texture: Slightly rough and hairy, not waxy or smooth.
Color: Same as stem, dark green, brownish green, JHS 3502, near RHS-145D.

Reproductive Organs

Stamen:
*Average length.*—0.5 mm.
*Average diameter.*—0.4 mm.
*Number per flower.*—4.
Pistil:
*Average length.*—0.6 mm.
*Average diameter.*—0.5 mm.
*Number per flower.*—1.

Other Distinguishing Characteristics

Seeds are absent and have not been observed; however, they may simply be too rare to observe and collect for measurement.
Resistance to high salinity: Satisfactory.
Growth rate: two (2) times that of female parent, 'S-Hitoshi', 3.5 times that of male parent, wild *L. nodiflora* 'Iwadaresou'.

What is claimed is:

1. A new and distinct variety of *Lippia* plant named 'Campagna-Verde', substantially as described and illustrated herein.

* * * * *